United States Patent [19]
Baker

[11] 3,968,796
[45] July 13, 1976

[54] DENTAL SYRINGE

[75] Inventor: Ronald L. Baker, Florence, Ky.

[73] Assignee: Thomas G. Lutes, Fort Mitchell, Ky.; a part interest

[22] Filed: Sept. 23, 1974

[21] Appl. No.: 508,154

[52] U.S. Cl. .............................. 128/173.1; 128/239; 32/22
[51] Int. Cl.² ........................................ A61M 11/00
[58] Field of Search................ 128/173.1, 173, 224, 128/225, 229, 239, 247; 32/22, 60, 40; 239/587, 303, 337

[56] References Cited
UNITED STATES PATENTS

| 905,250 | 12/1908 | Truman | 128/173 R |
|---|---|---|---|
| 1,757,473 | 5/1930 | Pieper | 128/239 |
| 2,029,734 | 2/1936 | Meitzler | 128/224 |
| 2,919,072 | 12/1959 | Corley, Jr. | 239/587 |
| 3,393,676 | 7/1968 | Kummer et al. | 128/229 X |
| 3,401,691 | 9/1968 | Beu | 128/173.1 |
| 3,506,002 | 4/1970 | Maurer et al. | 128/173.1 |
| 3,511,235 | 5/1970 | Stram | 128/173.1 |

*Primary Examiner*—John D. Yasko
*Attorney, Agent, or Firm*—Wood, Herron & Evans

[57] ABSTRACT

A dental syringe having an angulated nozzle projecting from one end of a housing. Two coaxial valve operating buttons project from the other end of the housing and are axially operable to supply water, air or both to the nozzle. The operating buttons are connected to coaxial valves within the housing, one of the buttons and its valve being rotatable to change the angular position of the nozzle.

10 Claims, 4 Drawing Figures

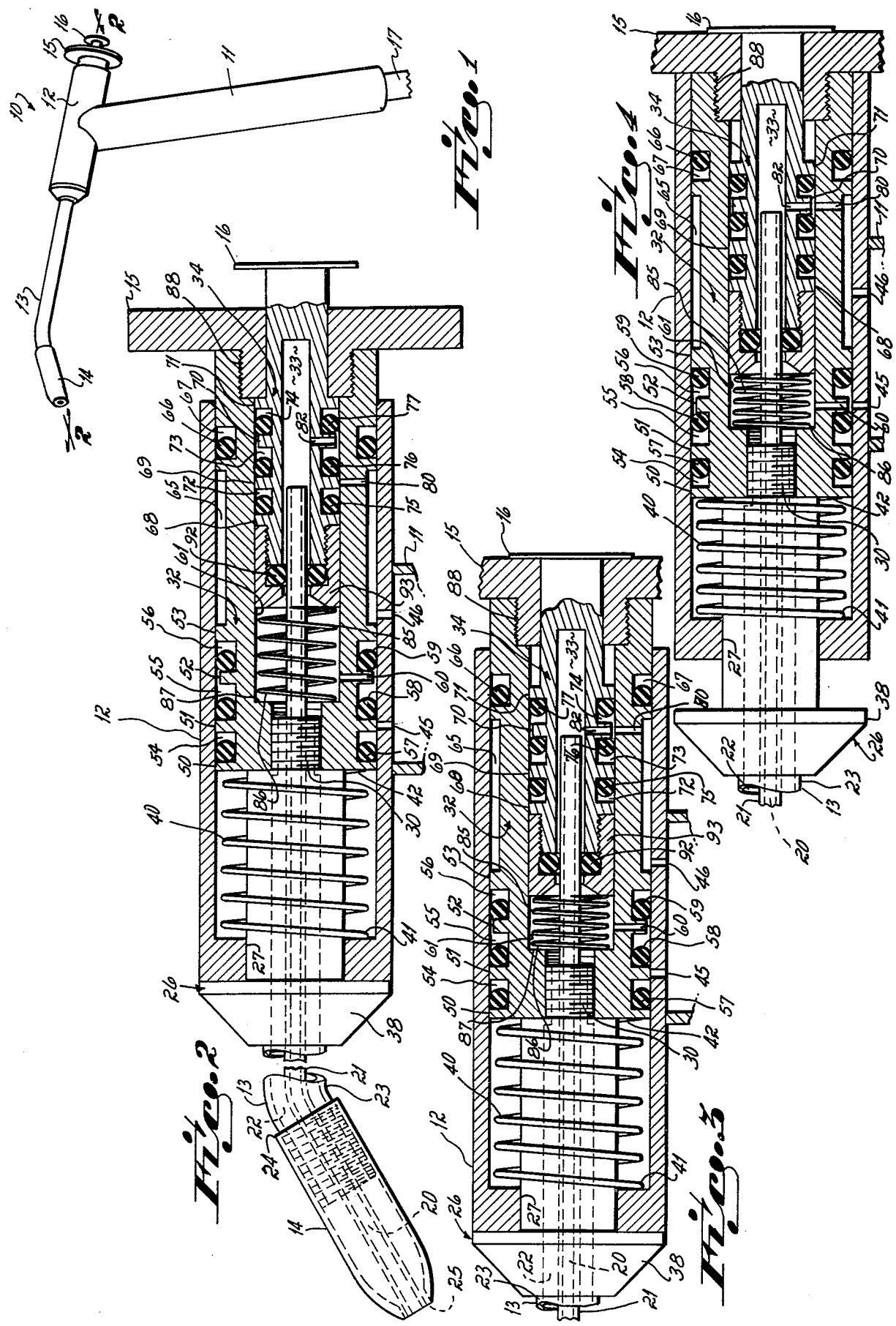

DENTAL SYRINGE

This invention relates to a dental syringe, and more particularly, the invention relates to a syringe having an angulated nozzle which is rotatable to improve its capability of directing fluids into the patient's mouth.

Dental syringes of different types are in common use. In general, each syringe has a housing, a nozzle and one or more valves with operating buttons which are adapted to selectively supply water, air or a combination of water and air to create a spray directed into the patient's mouth. The syringes usually have an angulated tip to permit the nozzle to be introduced into the patient's mouth with fluid being directed from the tip directly into a patient's tooth or gum. Preferably, the nozzle is rotatable so that the fluid can be conveniently aimed directly into the upper part or lower part of the patient's mouth.

Syringes with these attributes have valves within the housing and push buttons outside the housing to select the fluids or combinations of fluids. The nozzle is rotatably mounted on one end of the housing, and when the angular position of the nozzle is to be changed, the operator grasps the housing with one hand and the nozzle with the other to rotate the nozzle with respect to the housing. This arrangement has several disadvantages which the present invention seeks to overcome. First, it is necessary to contact the nozzle end of the syringe with the operator's hands, which contact tends to contaminate the nozzle with any bacteria which might be carried by the operator. Further, the rotation of the nozzle is necessarily a two-handed operation so that the operator must set aside other tools which he is using in order to make the adjustment. Still further, the need for grasping the nozzle to rotate it precludes the changing of the direction of the tip while it is in the patient's mouth. Thus, if the tip is not properly oriented, it is necessary to withdraw the syringe and make additional adjustments until it is properly oriented.

An objective of the present invention has been to provide a syringe having a nozzle with an angulated tip projecting from one end of the housing and having means for rotating the nozzle from the opposite end of the housing. The foregoing objective is accomplished in part by providing a housing, a nozzle projecting from one end of the housing and coaxial operating buttons projecting from the opposite end of the housing, one of the operating buttons being directly connected to the nozzle and being rotatable so that while the syringe is being grasped and operated, the nozzle can be rotated by the operator using only one hand.

The operating buttons are spring loaded, the outer button being smaller than the rotatable inner button. The outer button can be depressed to control one fluid, the inner button can be depressed to control the other fluid and both buttons can be depressed simultaneously to create a spray mixture of air and water to the nozzle tip.

The invention further contemplates the provision of a cylindrical housing having two coaxial spool valves to control the respective fluids. A first spool valve is axially movable to control a first fluid and is rotatable by an operating button to control the angular position of the nozzle. The second valve is located within an axial bore in the first valve and is axially operable to control the other fluid regardless of the axial or rotatable position of the first valve. Thus, with this combination the respective valves can be operated individually or jointly for the differing conditions of operation.

The several features and objectives of the present invention will become more readily apparent from the following detailed description taken in conjunction with the accompanying drawings in which:

FIG. 1 is a perspective view of a syringe of the present invention;

FIG. 2 is a cross sectional view of the syringe, partly in elevation, taken along lines 2—2 of FIG. 1;

FIG. 3 is a cross sectional view similar to that of FIG. 2 showing one of the valves in an operating position; and FIG. 4 is a view similar to FIG. 2 showing both of the valves in an operating position.

Referring to FIG. 1, a syringe 10 constructed in accordance with the present invention has a handle 11 secured to a cylindrical housing 12. A nozzle 13 having an angulated tip 14 projects from the front end of the housing 12. A large diameter air-operating button 15 projects from the rear end of the housing 12, and a water-operating button 16, coaxial with the air-operating button, projects rearwardly of the air-operating button 15. Tubing 17 which is connected to air and water, respectively, passes through the handle 11 and is connected to ports in the housing 12.

As best seen in FIG. 2, the nozzle 13 and tip 14 have a central passageway 20 for water defined by a tube 21 and an annular passageway 22 defined by a tube 23 surrounding the tube 21. A cap 24 threaded on the tube 23 forms a continuation of the tube 23 and terminates in a small opening 25 surrounding the end of the tube 21. The tubes 21 and 23 are joined together as an assembly 26 which is slidably mounted in a bore 27 at one end of the housing 12. The inner end of the assembly is threaded as at 30 and secured to a threaded bore at one end of a valve spool 32. The tube 21 projects inwardly beyond the tube 23 into a bore 33 of a second valve spool 34.

The assembly 26 includes a collar 38 secured to the tube 23 which lies across the end of the housing 12 and is of a frusto-conical configuration to provide a neat appearing assembly with the housing. The collar 38 defines the limit of inward movement of the assembly, that being the position in which the valve closes the supply of air, as will be described below. A compression spring 40 having one end 41 in engagement with the housing and the other end 42 in engagement with the spool 32 urges the spool 32 toward the closed position of FIGS. 2 and 3.

An air port 45 is formed in the housing wall and is connected to that portion of the supply tubing 17 which carries air to the syringe. A water port 46 is formed in the wall of the housing at a position spaced rearwardly from the air port. The water port is connected to that portion of the tubing 17 which delivers water to the syringe.

The supply of air is controlled by the position of the spool 32. The spool has four lands 50, 51, 52 and 53 defining three O-ring grooves 54, 55 and 56, each containing an O-ring 57, 58 and 59. The O-rings 57 and 58 define between them a valve "closed" area, and the O-rings 58 and 59 define between them a valve "open" area. The land 52 in the valve "open" area has one or more transverse bores 60 which connect the valve "open" area to a bore 61 which is in communication with the annular passageway 22 defined in part by the tube 23. When the spool 32 is in the position of FIG. 2, the air port 45 is surrounded by the two O-rings 57, 58, thereby sealing off the air port from the annular passageway 22. When the spool is shifted axially to the position of FIG. 4, the air port 45 is surrounded by the O-rings 58, 59 defining the valve "open" area and bringing the air port into communication with the transverse bore 60 to permit the flow of fluid from the air port 45 to the annular passageway 22 and out the end of the nozzle tip. The transverse bore 60 does not have to be in precise alignment with the air port 45 because the diameter of the land 52 is substantially smaller than the inside diameter of the housing, thereby creating a space between the housing and the land which permits air to flow all around the area defined between the two O-rings.

The spool 32 has an annular groove 65 which is always in communication with a water port 46, and hence water under pressure, regardless of the axial position of the spool 32. An O-ring 66 in an O-ring groove 67 at the rear end of the spool 32 seals the spool against leaking of the water at the rear end of the housing 12.

The spool 34 which is slidable in the bore 61 has four lands 68, 69, 70, 71 defining three O-ring grooves 72, 73 and 74 within which are disposed O-rings 75, 76, and 77. The O-rings 75 and 76 define between them a valve "closed" area and the O-rings 76 and 77 define between them a valve "open" area. The O-rings overlie one or more transverse water ports 80 connecting the annular groove 65 to the bore 61 of the spool 32. The land 70 has one or more transverse bores 82 between the two O-rings 76 and 77 which forms a communication between the valve "open" area and the bore 33 in the spool 34. When the spool 34 is in the axial position illustrated in FIG. 2 with respect to the spool 32, the water port 80 is surrounded by O-rings 75 and 76, thereby closing off the flow of water from the port 80 to the bore 82. When the spool 34 is shifted in a forward direction as illustrated in FIGS. 3 and 4, the port 80 is in communication with the valve "open" area between O-rings 76 and 77, thereby providing a communication between the port 80 through bore 82 to the bore 33 and the passageway 20 in tube 21, thereby permitting water to flow from the supply to the tube 21 and out the nozzle tip.

A compression spring 85 of a lower spring rate than spring 40 surrounds the projecting portion of the tube 21 and has one end 86 bearing on a shoulder 87 in the bore 61 and the other end bearing against the spool 34 to urge the spool outwardly.

The spool 32 is attached by a threaded connection 88 to the knurled operating button 15 by which the spool 32 is moved axially and by which the spool 32 is rotated to rotate the nozzle. The spool 34 projects beyond the rear end of the knurled button 15 and terminates in the button 16 by which the spool 34 is moved forwardly against the action of the compression spring 85. The rearward extent of movement of the spool 34 is fixed by the engagement of the rearmost land 71 against the inner extremity of the push button 15.

An O-ring 92 which is confined between the spool 34 and a cap 93 in the forward end of the spool 34 forms a water-tight seal between the spool and the projecting tube 21.

The operation of the invention is as follows:

In the condition shown in FIG. 2, no fluid flows since the air port 45 is closed by O-rings 57 and 58 and since the port 80 is closed by the O-rings 75 and 76. The operator grasping the syringe by the handle 11 may select one or both of the fluids by manipulating the push buttons 15 or 16. If water is selected, push button 16 is depressed to change its axial position from that illustrated in FIG. 2 to that illustrated in FIG. 3. The spring force of spring 40 is substantially greater than that of spring 85 so that when push button 16 is depressed to a limited extent, only spring 85 will be compressed. In the position shown in FIG. 3, the port 80 is embraced by the O-rings 76 and 77, thereby providing a communication to the bore 82 and hence bore 33 and passageway 20.

If only air is desired, the operator depresses only push button 15 to shift the spool 32 axially forward to bring the air port 45 into communication with the bore 60 as shown in FIG. 4. As not shown, however, the push button 16 would not have been depressed and, hence, the axial position of spool 34 with respect to spool 32 would not have changed.

When both water and air are desired, push button 16 is depressed to open the air port, and pressure is further applied against the push button 15 to shift both spools to the position shown in FIG. 4 where both the air port and water port are in communication with their respective annular passageway 22 and tubular passageway 20.

In any condition of operation, the nozzle 13 can be rotated and hence the angular position of the tip 14 changed with respect to the housing simply by rotating the knurled push button 15. The particular angular position of the knurled push button is not critical, for in any of its positions the axial orientation of the valve "closing" or valve "open" areas defined by the O-rings will remain unchanged.

The syringe may be cleaned or lubricated by a very simple disassembly procedure. The nozzle assembly 26 can be removed simply by rotating it with respect to the spool 32 and the spool 32 may then be withdrawn from the housing by pulling rearwardly on the push button 15. The spool 34 may be removed from the spool 32 simply by unscrewing push button 15 and thereafter pulling axially on the push button 15 while grasping the spool 32. Thus, all parts are exposed for cleaning, lubrication and any other maintenance operation which may be indicated.

Thus, the syringe of the invention has the desired operational controls consisting of two push buttons easily manipulated by the thumb of the operator with the capability of rotating the nozzle by rotating the knurled push button 15. Additionally, these attributes are achieved by a very simple mechanism which is easily manufactured and serviced.

What is claimed is:

1. A dental syringe comprising, a handle, a housing mounted on said handle, a nozzle rotatably mounted in and projecting from one end of said housing and having an angulated tip, an operator rotatably mounted at the other end of said housing, means connecting said operator to said nozzle to rotate said nozzle about its axis upon rotation of said operator to change the direction of said tip with respect to said handle, valve means in said housing, means for supplying air and water to said housing, the flow of said air and water to said nozzle being controlled by said valve means, said operator being axially slidable and connected to said valve means to control one of said fluids, a push button coaxial with said operator, said push button being axially slidable to and connected to said valve means to control the flow of said other fluid.

2. A dental syringe according to claim 1 in which said valve means comprises, a first spool rotatably and axially slidably mounted in said housing and connected to said operator, a second spool axially slidable in said first spool, and ports in said housing and spools to control the flow of fluids.

3. A dental syringe comprising, a housing connectable to supplies of water and air, a nozzle projecting from one end of said housing, valve means within said housing for controlling the flow of water and air, a first push button mounted for axial movement at the other end of said housing and operably connected to said valve means to control the flow of one of said fluids, a second push button coaxial with said first push button and axially spaced from said first push button, said second push button being axially movable with respect to said first push button and said housing, said second push button being operably connected to said valve means to control the flow of the other of said fluids to said nozzle.

4. A dental syringe as in claim 3 in which said push buttons are circular, said first push button having a larger diameter than said second push button.

5. A dental syringe as in claim 3 in which said push buttons, valve means and nozzle are rotatably mounted in said housing, said nozzle being rotatable by rotating said first push button.

6. A dental syringe comprising, a cylindrical housing, a nozzle projecting from said housing and having two fluid passageways therein, ports for air and water in the wall of said housing, an outer spool axially slidable in said housing and having a first position closing one of said ports and a second position providing a passageway between said one port and one of said nozzle passageways, an inner spool axially slidable within said outer spool, said inner spool having a first position closing the other of said ports and a second position providing a passageway between said other port and the other of said nozzle passageways.

7. A dental syringe as in claim 6 in which said water and air ports are axially spaced in said housing, said first spool having an axial bore connected to said nozzle, said first spool having axially spaced O-rings defining circumferential "closed" and "open" areas on said first spool, said first spool having a transverse bore connecting said open area to said bore, said first spool being axially shiftable between positions in which either said "open" or "closed" areas overlie said air port.

8. A dental syringe as in claim 7 in which said first spool has a circumferential groove overlying said water port and a transverse bore from said groove to said axial bore, said second spool being slidable in said first spool axial bore and having an axial bore connected to said other nozzle passageway, said second spool having axially spaced O-rings defining circumferential "closed" and "open" areas, said second spool having a transverse bore connected between said "open" area and its axial bore, said second spool being axially shiftable between positions in which either of its "open" or "closed" areas overlie said transverse bore between said groove and axial bore of said first spool.

9. A dental syringe as in claim 6 further comprising, a first spring between said housing and first spool urging said first spool away from said nozzle to its closed position, a second spring between said first spool and said second spool urging said second spool away from said nozzle to a closed position, said first spring having a greater spring rate than said second spring, and coaxial spaced push buttons connected to said first and second spools, respectively.

10. A dental syringe comprising, a cylindrical housing, a nozzle projecting from one end of said housing and having an angulated tip, axially spaced ports in the wall of said housing connectable to supplies of water and air, a first spool mounted in said housing for rotary and axial movement, said spool being fixed to said nozzle and having a push button projecting from the opposite end of said housing, a spring in said housing urging said spool axially to a first position closing one of said ports, said spool being slidable to a second position to open a passageway from said one port to said nozzle, said spool being rotatable to any position by rotating said push button to change the direction of said nozzle tip, said first spool having an axial bore, a second spool mounted in said bore for axial sliding movement, said second spool having a first axial position blocking fluid flow from said second port and a second position permitting flow from said second port to said nozzle, and a spring in said axial bore urging said second spool to said first position.

\* \* \* \* \*